(12) United States Patent
Vaillancourt et al.

(10) Patent No.: US 6,841,357 B1
(45) Date of Patent: Jan. 11, 2005

(54) METHOD AND KITS FOR TITERING ADENO-ASSOCIATED VIRUS VECTORS

(75) Inventors: Peter Edward Vaillancourt, Del Mar, CA (US); Vivian Qingqing Zhang, San Diego, CA (US)

(73) Assignee: Stratagene California, La Jolla, CA (US)

( * ) Notice: Subject to any disclaimer, the term of this patent is extended or adjusted under 35 U.S.C. 154(b) by 324 days.

(21) Appl. No.: 10/113,547

(22) Filed: Mar. 29, 2002

Related U.S. Application Data

(60) Provisional application No. 60/280,228, filed on Mar. 30, 2001.

(51) Int. Cl.[7] .................................................. C12Q 1/02
(52) U.S. Cl. ............................ 435/29; 435/4; 435/975
(58) Field of Search ............................... 435/29, 4, 975

(56) References Cited

U.S. PATENT DOCUMENTS 6,566,118 B1 * 5/2003 Atkinson et al. ........... 435/239
6,703,237 B2 * 3/2004 Samulski et al. ......... 435/320.1

OTHER PUBLICATIONS

Xiao Xiao et al; Production of High–Titer Recombinant Adeno–Associated Virus Vectors in the Absence of Helper Adenovirus; Journal of Virology, Mar. 1998, p. 2224–2232.

T. Matsushita et al; Adeno–associated virus vectors can be efficiently produced without helper virus; Gene Therapy (1998) 5, 938–945.

* cited by examiner

*Primary Examiner*—Louise N. Leary
(74) *Attorney, Agent, or Firm*—Kathleen M. Williams; Palmer & Dodge LLP

(57) ABSTRACT

A method of titering adeno-associated virus particles in a sample, said method comprising the steps of contacting target cells with a DNA synthesis inhibitor and an agent that increases the activity of the CMV immediate early promoter; contacting target cells treated as in step (a) with a sample containing adeno-associated virus particles; and determining the number of target cells infected by said adeno-associated virus particles in said sample, wherein said number of target cells infected is directly proportional to the titer of said particles in said sample, thereby determining the titer if said adeno-associated virus particles.

48 Claims, 5 Drawing Sheets

Production of recombinant AAV particles

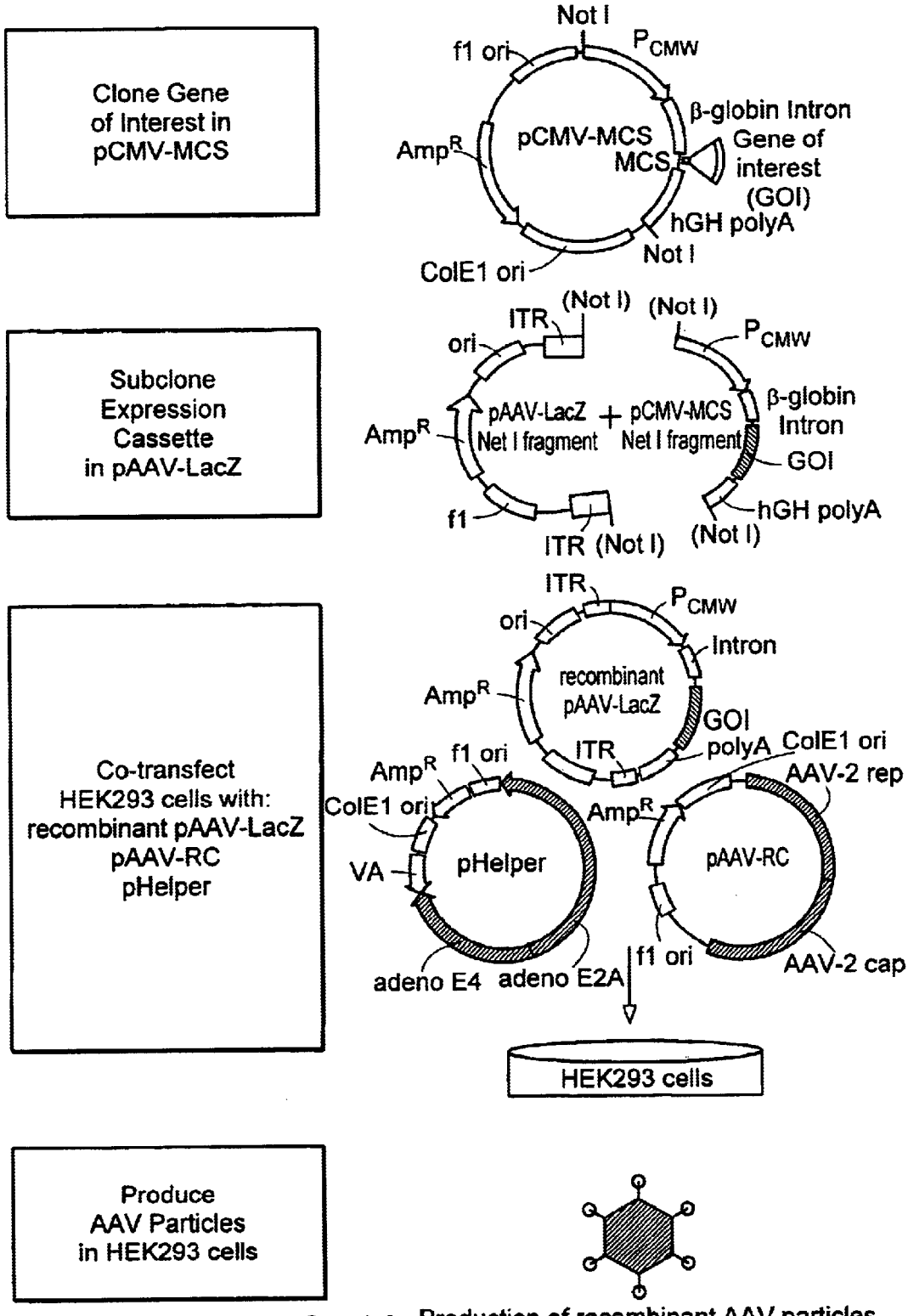
FIG. 1A  Production of recombinant AAV particles

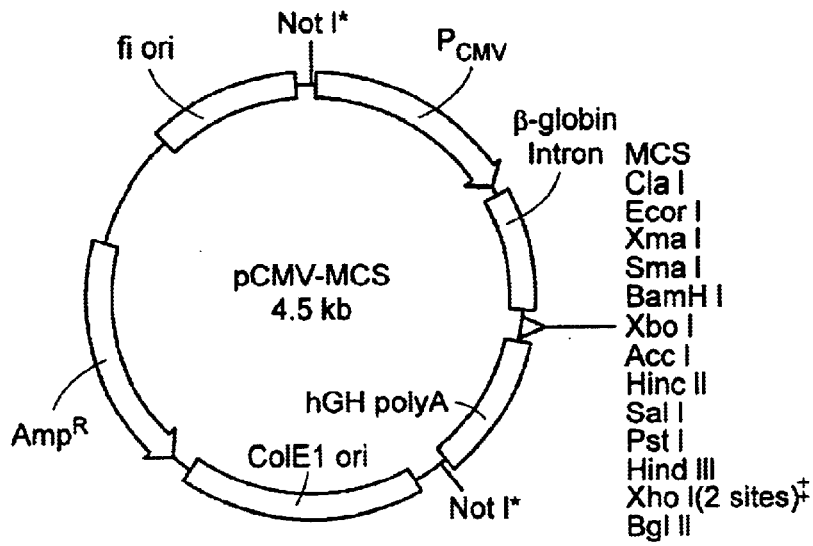

*Non-unique sites used to release the expression cassette
‡The two Xho I sites are adjacent in the MCS and are suitable for use in cloning pCMV-MCS Multiple Cloning Site (1178-1253)

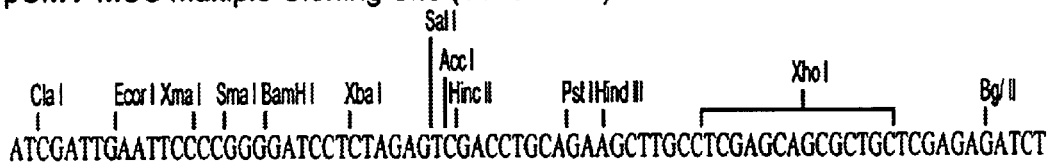

| Feature | Nucleotide Position |
|---|---|
| CMV promoter | 1-670 |
| β-globin Intron | 678-1170 |
| MCS | 1178-1253 |
| human growth hormone (hGH) polyadenylation signal | 1249-1735 |
| ColE1 replication origin | 1844-2701 |
| ampicillin resistance gene (Amp$^R$) | 2711-3571 |
| f1 origin of replication | 3952-4413 |
| Not I cleavage sites | 2, 1765 |

FIG. 1B

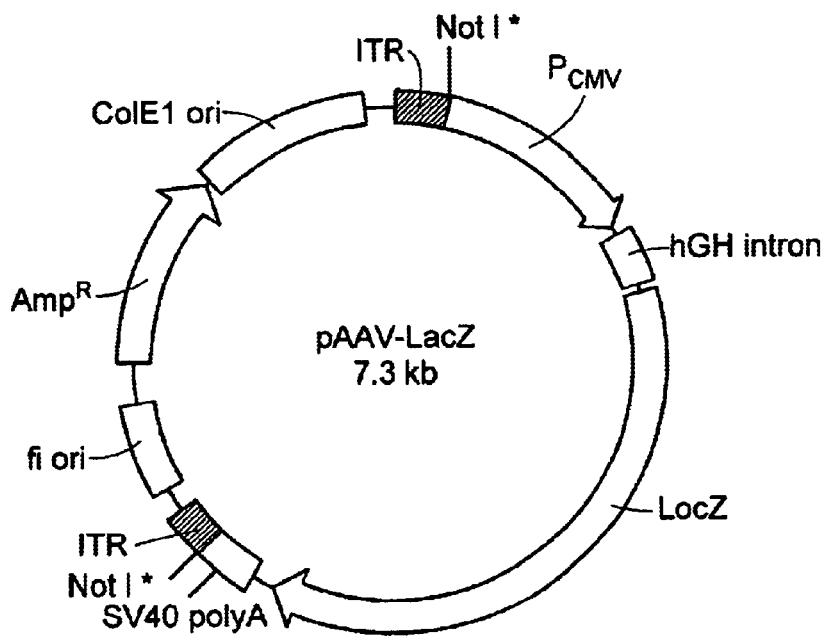

*Sites used to release and subclone expression cassette

| Feature | Nucleotide Position |
|---|---|
| left AAV-2 inverted terminal repeat (ITR) | 1-145 |
| CMV promoter | 150-813 |
| human growth hormone (hGH) intron I | 817-1087 |
| β-galactosidase (LacZ) gene | 1093-4346 |
| SV40 early polyadenylation signal | 4361-4506 |
| right AAV-2 inverted terminal repeat (TTR) | 4526-4668 |
| f1 origin of replication | 4749-5209 |
| ampicillin resistance gene (Amp$^R$) | 5591-6451 |
| ColE1 replication origin | 6463-7271 |
| Not I cleavage sites | 143, 4527 |

FIG. 1C

| Feature | Nucleotide Position |
|---|---|
| AAV-2 rep gene | 129-1996 |
| AAV-2 cap gene | 2013-4346 |
| f1 origin of replication | 4705-5161 |
| ampicillin resistance gene (Amp$^R$) | 5292-6152 |
| ColE1 replication origin | 6162-7019 |

| Feature | Nucleotide Position |
|---|---|
| adenovirus-5 E2A gene | 1-5336 |
| adenovirus-5 E4 gene | 5336-8537 |
| adenovirus-5 VA gene | 8537-9280 |
| ColE1 replication origin | 9315-10167 |
| ampicillin resistance gene (Amp$^R$) | 10182-11042 |
| f1 origin of replication | 11172-11627 |

METHOD AND KITS FOR TITERING ADENO-ASSOCIATED VIRUS VECTORS

RELATED APPLICATIONS

This application claims the benefit of U.S. Provisional Application No. 60/280,228, filed on Mar. 30, 2001, the entirety of which are incorporated herein by reference.

FIELD OF THE INVENTION

The invention relates to the field of viral vectors useful for gene transduction and gene therapy. More specifically, the invention relates to methods and kits for determining the titer of adeno-associated virus vector preparations.

BACKGROUND OF THE INVENTION

Adeno-associated viruses (AAVs) are replication deficient parvoviruses which require helper virus co-infection for productive infection. The human adeno-associated virus-2 (AAV-2) based vectors have been used as gene delivery vehicles in gene therapy.

The human adeno-associated virus-2, a member of the parvovirus family, is one of the smallest animal DNA viruses. The linear, single-stranded DNA genome of AAV-2 is 4.8 kilobases (kb) in length and encodes replication (rep) and capsid (cap) genes, which are flanked by inverted terminal repeats (ITRs) at both ends. The rep gene encodes four proteins that are directly involved in viral gene expression and AAV replication. The cap gene has three structural protein products: VP1; VP2; and VP3. The AAV ITRs, the only sequences required in cis, are responsible for DNA replication, packaging and integration.

AAV-2, except under specific conditions (e.g., stress-causing agents, such as U.V. irradiation), is naturally replication defective and requires co-infection with an unrelated helper virus, e.g., adenovirus or herpesvirus, for productive infection in a host cell. This feature, along vectors have additional advantages: the virus transduces not only dividing cells but also non-dividing cells; the virus has a broad host cell range; the virus establishes long term gene expression; and the virus generates high titer AAV vector particles that do not need to be concentrated. Properties of AAV based vectors are compared with those of retroviral and adenoviral based gene delivery vectors in Table 1.

TABLE 1

Comparison of AAV, Adenovirus and Retrovirus-based gene delivery vector systems

| Viral types | Adeno-associated virus | Adenovirus | Retrovirus |
| --- | --- | --- | --- |
| Host: dividing cells | Yes | Yes | Yes |
| Host: non-dividing cells | Yes | Yes | No |
| Integration | Yes | No | Yes |
| Long-term expression | Yes | No | No |
| High titer viral production | High | High | Low |
| Host immunogenicity | Low | High | Low |

The AAV-based vectors offer numerous advantages over other viral based systems, but until recently, difficulty in producing vector particles has been a drawback.

Production of AAV Particles

The original method of producing recombinant AAV vector particles involved co-transfection of two separate plasmids into cells (e.g., 293 cells) followed by infection of the cells with adenovirus. One plasmid encoded a gene of interest flanked by AAV ITRs, and the second plasmid encoded the AAV rep and cap genes without the AAV ITRs. Infection of the co-transfected cells with adenovirus supplied in trans the replication factors necessary for AAV particle production, and both recombinant AAV particles and adenovirus particles were produced, usually over a period of about 72 hours. The AAV particles were separated from the adenovirus particles following an incubation at 56° C. to inactivate adenoviruses, followed by one or two rounds of preparative cesium chloride ultracentrifugation. See Matsushita et al, 1998, Gene Therapy 5: 938–945, incorporated herein by reference.

This original method of preparing AAV particles was laborious and inefficient, with reductions in the titer of infective AAV particles at each purification step. Even after purification, functional adenovirus contamination remained a possibility and preparations were always contaminated with adenovirus structural proteins that could trigger host immune responses. These drawbacks led to the development of an adenovirus-free AAV production system.

In the original adenovirus-free system, introduced in 1998, the adenovirus genes necessary for AAV replication (adenoviral VA, E2A, 72-$M_r$ and E4orf6 genes and the E1 region) were identified and all the genes except E1 were assembled into a helper vector. This helper vector was missing some of the early and many of the late adenovirus genes, and could not by itself produce infectious adenovirus. To produce AAV particles in the absence of adenovirus, a three-way co-transfection into cells expressing E1 was performed. The three plasmids were the helper plasmid, an AAV plasmid encoding a gene of interest flanked by AAV ITRS, and a plasmid encoding the AAV rep and cap genes without the AAV ITRs (see FIG. 1; Matsushita et al., 1998, supra, and Xiao et al., 1998, J. Virol. 72: 2224–2232, incorporated herein by reference).

The triple-plasmid helper-free system is as efficient as the original system employing wild-type adenovirus. The AAV particles produced in the helper virus free AAV system and in the traditional AAV system have the same viral particle density, particle-to-infectivity ratio, capsimer ratio and transduction efficiency in vivo. Unlike particles made using helper virus, however, particles made in the helper virus-free AAV system do not react with anti-adenovirus sera Matsushita et al, 1998, supra).

Titering AAV Stocks

For many applications of AAV vectors it is necessary to determine the viral titer (i.e., the number of infectious viral particles per unit volume) of the recombinant AAV stock. AAV infection is generally measured in one of three ways: 1) a "reporter" virus produced in parallel with the AAV particles carrying the gene of interest produces a measurable marker polypeptide; 2) a reporter gene expressed from the same AAV vector that expresses the gene of interest produces a marker polypeptide; or 3) the level of the gene of interest is measured directly, e.g., by antibody staining. To determine the titer, a small portion of the virus preparation is used to infect a target tissue culture cell-type, the cells are examined for reporter expression, and the titer is calculated based on the proportion of cells that express the reporter. In this approach, a serious drawback is the relatively lengthy time period, 7–10 days or more, required for the accumulation of a suitable quantity of reporter protein (often green fluorescent protein or β-galactosidase) in the cell.

In order to decrease the time required to obtain AAV titer results, wild-type adenovirus has been used. The adenovirus infection supplies in trans the replication factors necessary to boost the reporter signal and/or to enhance the efficiency of AAV viral transduction. Although titering by co-infection with adenovirus typically reduces the required time until reporter analysis to 2–3 days, variation in the relative efficiency of infection by AAV and adenovirus from cell line to cell line results in variable titer values. This method also requires the use of wild-type adenovirus, which is undesirable to many researchers and clinicians. There is a need in the art for improved methods of titering AAV stocks.

SUMMARY OF THE INVENTION

The invention provides improved methods of determining the titer of infectious AAV vector particles. The methods provided do not require the use of any helper virus, thereby eliminating variations in target cell susceptibility to adenovirus infection and avoiding the problems inherent in the use of infectious adenoviruses. The methods provided also decrease the time necessary to determine AAV titers relative to standard methods.

The invention encompasses a method of titering adeno-associated virus particles in a sample, the method comprising the steps of: a) contacting target cells with a DNA synthesis inhibitor and an agent that increases the activity of the CMV immediate early promoter, b) contacting target cells treated as in step (a) with a sample containing adeno-associated virus particles; and c) determining the number of target cells infected by the adeno-associated virus particles in the sample, wherein the number of target cells infected is directly proportional to the titer of the particles in the sample, thereby determining the titer of the adeno-associated virus particles.

In one embodiment, the target cells are not infected with adenovirus.

In another embodiment, the DNA synthesis inhibitor is selected from the group consisting of: hydroxyurea and aphidicolin.

In another embodiment, the DNA synthesis inhibitor is hydroxyurea.

In a preferred embodiment, the hydroxyurea is present in step (b) at a concentration in the range of 20 mM to 80 mM, inclusive. It is further preferred that the hydroxyurea is present in step (b) at a concentration of 40 mM.

In another embodiment, the agent that increases the activity of the CMV immediate early promoter is selected from the group consisting of: sodium butyrate, dibutyryl cAMP, forskolin phytohaemagglutinin (PHA), and phorbol-12-myristate-13-acetate (PMA).

In a preferred embodiment, the agent that increases the activity of the CMV immediate early promoter is sodium butyrate. It is further preferred that the sodium butyrate is present in step (b) at a concentration in the range of 0.2 mM to 2.0 mM, inclusive. It is further preferred that the sodium butyrate is present at a concentration of 1 mM.

In another embodiment, the DNA synthesis inhibitor is hydroxyurea and the agent that mcreases the activity of the CMV immediate early promoter is sodium butyrate. It is preferred that the hydroxyurea is present in step (b) at a concentration in the range of 20 mM to 80 mM, inclusive, and the sodium butyrate is present in step (b) at a concentration in the range of 0.2 mM to 2.0 mM, inclusive. It is further preferred that the hydroxyurea is present in step. (b) at a concentration of 40 mM and the sodium butyrate is present at a concentration of about 1 mM In another embodiment, after step (a) and before step (b) of the method described above, the DNA synthesis inhibitor and the agent that increases the activity of the CMV immediate early promoter are substantially removed.

The invention further encompasses a method of titering adeno-associated virus particles in a sample, the method comprising the steps of: a) contacting target cells with a topoisomerase inhibitor and an agent that increases the activity of the CMV promoter; b) contacting target cells treated as in step (a) with a sample containing adeno-associated virus particles; and c) determining the number of target cells infected by the adeno-associated virus particles in the sample; wherein the number of target cells infected is directly proportional to the titer of the particles in the sample, thereby determining the titer of the adeno-associated virus particles.

In one embodiment, the target cells are not infected with adenovirus.

In another embodiment, the topoisomerase inhibitor is selected from the group consisting of: etoposide, camptothecin, amsacrine and novobiocin. It is preferred that the topoisomerase inhibitor is etoposide. It is further preferred that the etoposide is present in step (b) at a S concentration in the range of 0.5 $\mu$M to 5.0 $\mu$M, inclusive. It is further preferred that the etoposide is present at a concentration of 3 $\mu$M.

In another embodiment, the agent that increases the activity of the CMV immediate early promoter is selected from the group consisting of. sodium butyrate, dibutyryl cAMP, forskolin phytohaemagglutinin (PHA), and phorbol-12-myristate-13-acetate PMA), and phorbol-12-myristate-13-acetate (PMA). It is preferred that the agent that increases the activity of the CMV immediate early promoter is sodium butyrate. It is further preferred that the sodium butyrate is present in step (b) at a concentration in the range of 0.2 $\mu$M to 2.0 mM, inclusive. It is further preferred that the sodium butyrate is present in step (b) at a concentration in the range of 1 mM.

In another embodiment, the topoisomerase inhibitor is etoposide and the agent that increases the activity of the CMV immediate early promoter is sodium butyrate.

In a preferred embodiment, the hydroxyurea is present in step (b) at a concentration in the range of 0.2 mM to 80 mM, inclusive, and the sodium butyrate is present in step (b) at a concentration in the range of 0.2 mM to 2.0 mM, inclusive. It is further preferred that the hydroxyurea is present at a concentration of about 40 mM and the sodium butyrate is present at a concentration of 1 mM.

In another embodiment, after step (a) and before step (b) in the method described above, the DNA synthesis inhibitor and the agent that increases the activity of the CMV immediate early promoter are substantially removed.

The invention further encompasses a kit for determining the titer of AAV vector particles in a sample, the kit comprising a DNA synthesis inhibitor, an agent that increases the activity of the CMV immediate early promoter, and packaging materials therefor.

In one embodiment, the DNA synthesis inhibitor is selected from the group consisting of: hydroxyurea and aphidicolin.

In another embodiment, the DNA synthesis inhibitor is hydroxyurea.

In another embodiment, the agent that increases the activity of the CMV immediate early promoter is selected from the group consisting of: sodium butyrate, dibutyryl cAMP, forskolin phytohaemagglutinin (PHA), and phorbol-12-myristate-13-acetate (PMA).

In another embodiment, the agent that increases the activity of the CMV immediate early promoter is sodium butyrate.

The invention further encompasses a kit for determining the titer of AAV vector particles in a sample, the kit comprising an AAV vector system, a DNA synthesis inhibitor, an agent that increases the activity of the CMV immediate early promoter and packaging materials therefor.

In one embodiment, the DNA synthesis inhibitor is selected from the group consisting of: hydroxyurea and aphidicolin. It is preferred that the DNA synthesis inhibitor is hydroxyurea In another embodiment, the agent that increases the activity of the CMV immediate early promoter is selected from the group consisting of sodium butyrate, dibutyryl cAMP, forskolin phytohaemagglutinin (PHA), and phorbol-12-myristate-13-acetate (PMA). It is preferred that the agent that increases the activity of the CMV immediate early promoter is sodium butyrate.

The invention further encompasses a kit for determining the titer of an AAV vector particle in a sample, the kit comprising a topoisomerase inhibitor, an agent that increases the activity of the CMV immediate early promoter and packaging materials therefor.

In one embodiment, the topoisomerase inhibitor is selected from the group consisting of: camptothecin and etoposide.

In another embodiment, the topoisomerase inhibitor is etoposide.

In another embodiment, the agent that increases the activity of the CMV immediate early promoter is selected from the group consisting of sodium butyrate, dibutyryl cAMP, forskolin phytohaemagglutinin (PHA), and phorbol-12-myristate-13-acetate (PMA).

In another embodiment, the agent that increases the activity of the CMV immediate early promoter is sodium butyrate.

The invention further encompasses a kit for determining the titer of an AAV vector particle in a sample, the kit comprising an AAV vector system, a topoisomerase inhibitor, and an agent that increases the activity of the CMV immediate early promoter.

In a preferred embodiment, the topoisomerase inhibitor is selected from the group consisting of camptothecin and etoposide. It is preferred that the topoisomerase inhibitor is etoposide.

In another preferred embodiment the agent that increases the activity of the CMV immediate early promoter is selected from the group consisting of sodium butyrate, dibutyryl cAMP, forskolin phytohaemagglutinin (PHA), and phorbol-12-myristate-13-acetate (PMA). It is preferred that the agent that increases the activity of the CMV immediate early promoter is sodium butyrate.

As used herein, the term "adeno-associated virus particles" refers to human parvovirus particles that are dependent upon co-infection with adenovirus (e.g., Ad5) for productive infection. Productive infection refers to an infection in which the AAV replicates to form new viral particles. Productive infection is to be contrasted with and does not encompass infection or functional infection, in which the AAV particle delivers its nucleic acid to the host or target cell but does not replicate viral particles within that cell. Generally, AAV gene transduction vectors are based on the AAV strain AAV-2 (genome sequence available at GenBank Accession No. NC 001401), but any known AAV strain can be used to prepare AAV virus particles to be titered according to the methods of the invention.

As used herein, the term "titer" refers to both the process of determining the number of infectious viral particles in a sample and to the resulting number itself.

As used herein, the term "DNA synthesis inhibitor" refers to an agent that decreases the incorporation of $^3$H-thymidine into DNA in cultured cells by at least 10% relative to the incorporation in the absence of that agent. Alternatively, or in addition, a DNA synthesis inhibitor is an agent that reduces DNA synthesis as measured by pulse labeling with tritiated thymidine and scintillation counting of acid precipitable counts at least 50% as well as 40 mM hydroxyurea, in a given cell type. Tritiated thymidine incorporation can alternatively be measured by autoradiography.

As used herein, the term "topoisomerase inhibitor" refers to an agent that decreases the activity of a topoisomerase in a sample by at least 10% relative to a sample without that agent, wherein topoisomerase activity is assayed by measuring the relaxation of supercoiled pBR322 plasmid at 37° C. for 30 minutes and relaxation is detected by gel electrophoresis. Alternatively, or in addition, a topoisomerase inhibitor is an agent that decreases the activity of a topoisomerase at least 50% as well as 3 $\mu$M etoposide in a culture of a given cell type. Methods of measuring topoisomerase activity are known in the art and described herein below.

As used herein, the term "agent that increases the activity of the CMV immediate early promoter" refers to an agent that increases the expression of a detectable marker from a CMV promoter-driven construct in a transient transfection assay by at least 10%, relative to a parallel culture without that agent. As used in this definition, the transient transfection assay for monitoring CMV promoter activity uses approximately 50% confluent HT1080 cells in 100 mm tissue culture dishes transfected by the calcium phosphate method with 25 $\mu$g of a CMV major immediate early promoter driven nucleic acid construct. Calcium phosphate transfection is described in *Short Protocols in Molecular Biology,* Ausubel et al., Eds., John Wiley & Sons, Inc., 3$^{rd}$ Edition, 1995, pp 9–5 to 9–6. Agents being tested for activity on the CMV promoter are added immediately after the calcium phosphate precipitate is removed, and the accumulation of detectable marker is measured at 48 hours after transfection with an assay appropriate for the detectable marker used. CMV major immediate early promoter activity can be measured using a construct wherein the CMV major immediate early promoter is operatively linked to a detectable marker gene and a eukaryotic polyA site. The CMV major immediate early promoter is contained within the viral genome sequence −299 to +69, numbered according to the convention of Akrigg et al., 1985, Virus Res. 2: 107–121, incorporated herein by reference. Useful detectable markers include, for example, *E. coli* lacZ, chloramphenicol acetyltransferase, luciferase, green fluorescent protein, alkaine phosphatase, etc.

As used herein, the term "target cell" refers to a cell that can be infected with an AAV vector particle. By infection is meant a functional infection, not necessarily a productive (i.e., replicative) infection.

As used herein, the term "directly proportional" refers to the existence of a known linear relationship between the number of infected cells detected in a titer assay and the number of infectious particles present in a tested virus stock.

As used herein, the term "transduction efficiency" is an expression of the proportion of cells that express or transduce a transgene when a cell culture is contacted with AAV vector particles. The efficiency can be expressed as the number of cells expressing a transgene when a given number of cells are contacted with a given number of AAV vector particles as taught by Russell et al., 1995, Proc. Natl. Acad. Sci. U.S.A. 92: 5719–5723. "Relative transduction efficiency" is the proportion of cells transduced by a given number of viral particles in one culture relative to the proportion of cells transduced by that same number of particles in another culture comprising a similar number of cells of the same cell type and in the same proliferative state as the first culture. Relative transduction efficiency is most often used to compare the effects of a modulator of transduction efficiency on a culture treated or not treated with that modulator.

As used herein, the term "increase in relative transduction efficiency" means that the transduction efficiency of a given cell type by an AAV vector particle is increased by at least 10% in the presence of a given agent relative to the transduction efficiency with the same amount of AAV vector particles in the absence of that agent, when transduction is performed as taught by Russell et al., 1995, supra.

As used herein, the term "substantially removed" refers to the removal of one or more DNA synthesis inhibitors, topoisomerase inhibitors and/or agents that stimulate CMV promoter activity in a culture to the point where any residual concentration of an agent is no longer able to exert the inhibitory or stimulatory effect of the agent. The concentration at which a given agent no longer exerts an inhibitory effect on DNA synthesis, topoisomerase activity and/or CMV promoter activity is the concentration at which the rate of, e.g., DNA synthesis or topoisomerase activity, is at least 90%, preferably 95%, 96%, 97%, 98%, 99% or even 100%, of the rate of that process in cells not treated with that agent. The concentration at which a given agent no longer exerts a stimulatory effect on CMV promoter activity is the concentration at which the rate of CMV promoter activity is increased by no more than 2%, and preferably by no more than 1%, 0.1%, 0.001% or not at all relative to the rate of the process in cells not treated with that agent. Assays to measure DNA synthesis, topoisomerase activity and CMV promoter activity according to this definition are those set forth above for measuring these respective activities in the definitions of "DNA synthesis inhibitor," "topoisomerase inhibitor" and "agent that increases the activity of the CMV promoter." One of skill in the art can routinely test reagents such as DNA synthesis inhibitors, topoisomerase inhibitors and agents that stimulate CMV promoter activity for their effects in a given target cell.

As used herein the term "AAV vector system" refers to a collection of recombinant nucleic acid vectors that permit the production of AAV particles as they are defined herein above. An AAV vector system as the term is used herein will not comprise a wild-type adenovirus or other helper virus. That is, an AAV vector system is "helper free."

BRIEF DESCRIPTION OF THE FIGURES

FIG. 1 A–E shows schematic diagrams of the vectors comprising the helper-free AAV system used to generate AAV particles titered according to the methods of the invention FIG. 1A shows schematically how the pCMV-MCS vector is used to generate a CMV-promoter-driven gene of interest (GOI) cassette that is then used to replace the lacZ gene in the the AAV vector pAAV-LacZ, to generate a recombinant pAAV vector encoding the GOI. The AAV-GOI construct is co-transfected with pHelper and pAAV-RC, which encode adenovirus helper functions and AAV rep and cap, respectively, into HEK293 cells to produce recombinant AAV particles. FIG. 1B shows a more detailed schematic of the pCMV-MCS cloning vector used to make the CMV-GOI cassette. FIG. 1C shows a more detailed schematic of the pAAV-LacZ vector.

DESCRIPTION OF THE INVENTION

The invention relates to methods and kits for determining the titer of AAV particles. The methods and kits of the invention provide AAV titer information without the need for helper virus of any kind. The titer information provided by these methods and kits is rapid, requiring only about two days.

To titer AAV stocks according to the invention, target cells, such as HT1080 cells, are pre-treated with a DNA synthesis or topoisomerase inhibitor and with an agent that increases the activity of the CMV major immediate early promoter. The pre-treated cells are then exposed to known dilutions of sample containing AAV particles to be titered. After time sufficient to permit the expression of a detectable marker, usually about two days, the cultures are processed to detect cells that have transduced the AAV vector sequence. The number of cells transducing the vector sequence is then used, with the known dilution factor, to determine the number of infectious AAV particles present in the original stock sample.

The individual steps and considerations affecting the performance of each of these steps are described in more detail below.

Producing AAV Vector Particles

Any system known in the art may be used to produce AAV particles that can be titered using the methods of the invention For example, one can use the standard method described above in which two vectors, one encoding a gene of interest flanked by AAV ITRs and another encoding AAV rep and cap genes, are co-transfected into cells that are then infected with wild type adenovirus as helper. Alternatively, one may use the helper virus-free methods described by Matsushita et al. (1998, supra) and Xiao et al. (1998, supra).

Figure 1D:
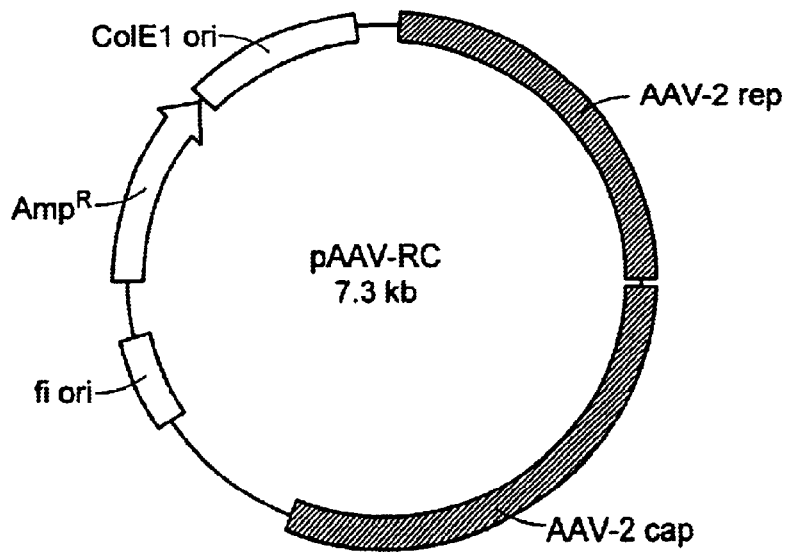
FIG. 1D shows a more detailed schematic of the pAAV-RC vector.
Figure 1E:
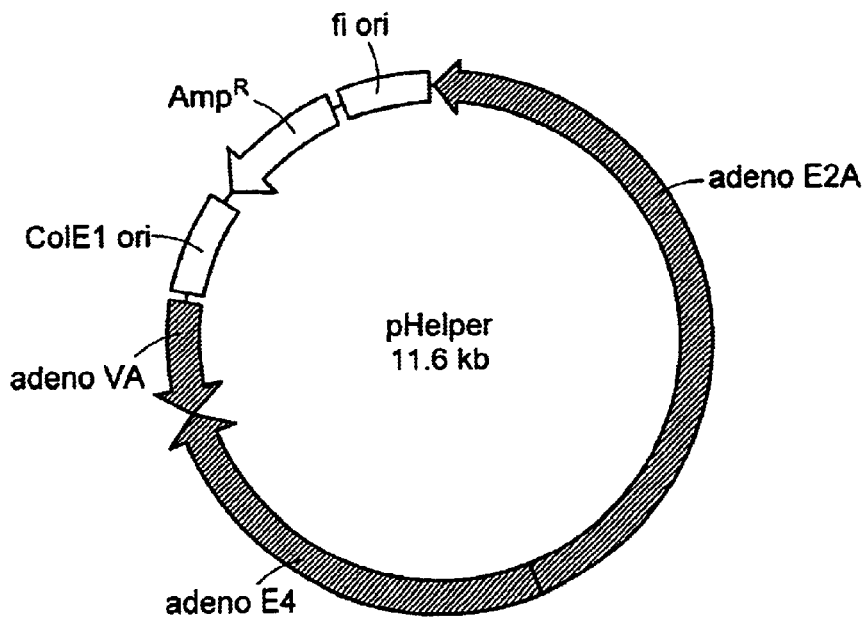
FIG. 1E shows a more detailed schematic of the pHelper vector.

A preferred method of producing AAV particles comprises four vectors, shown in the diagrams of FIG. 1, A–E: p4.1c, pVmLacZ, pHLP19 and pladeno 5. The commercial names of these four vectors are pCMV-MCS, pAAV-LacZ, pAAV-RC and pHelper, respectively (available from Avigen, Alameda, Calif.). The first two vectors, p4.1c and pVmLacZ are cloning vectors: The p4.1c vector has a multiple cloning site for introducing a gene of interest (e.g., a marker gene or a potentially therapeutic transgene), as well as a CMV promoter, an intron sequence and a poly-A site. The p4.1c vector lacks AAV ITRs, but possesses all elements necessary for transgene expression in mammalian cells. The expression cassette in the p4.1c is cut out by restriction enzyme NotI digestion and used to replace the lacz gene in the pVmLacZ vector. The pVmLacZ vector has two ITRs, and the region carrying both ITRs is flanked on one end by a recognition sites for the restriction enzyme NotI and on the other by a site for Sse 8387. The pVMLacZ vector, which expresses β-galactosidase can also be used as a control vector. The double cloning steps described here allow for manipulations such as site-directed mutagenesis to be performed in the more stable p4.1c vector. If such manipulations were performed directly in a vector bearing ITRs, recombination between the ITRs could cause problems. The pHLP19 plasmid encodes rep and cap genes of AAV-2. The pladeno 5 plasmid encodes adenovirus-5 genes required to support AAV replication in the absence of helper virus. It has been observed that AAV rep and cap genes have different effects on AAV vector production (Li et al., 1997, J. Viral, 71: 5236–5242; Vincent et al, 1997, J. Viral, 71: 1897–1905): up-regulation of cap gene results in higher AAV vector titer, however, the rep gene product inhibits cap gene expression, resulting in reduced AAV vector titer. In the Avigen AAV system, the rep and cap gene expression levels are optimized under different promoters to achieve high titer production of AAV.

In order to produce AAV viral vector particles, cells expressing E1(e.g., 293X cells) are evenly seeded at a density of $3 \times 10^6$ per 10 cm plate containing 10 ml of medium, and cultured for 48 hours. Cells are then transfected with the three vectors of the AAV: system: pladeno 5, pHLP19 and the construct made by placing the transgene expression cassette into the ITR-containing vector.

Any transfection method known in the art to be suitable for the cell type being used is acceptable, but calcium phosphate transfection works well. Exemplary calcium phosphate transfection conditions are as follows. One ml of 0.3M $CaCl_2$ is added to a 15-ml conical tube with 30 µg of plasmids (10 µg each of pHLP19, pladeno 5 and pVmLacZ or pVmhrGFP), mixed gently and the mixture is added drop-wise to another 15-ml tube containing 1 ml of 2×HBS (280 mM NaCl, 50 mM HEPES, 1.5 mm $NaPO_4$, NaOH to pH7.1 exactly), and mixed gently by inversion or gentle vortexing. The suspension is immediately applied drop-wise to the plate without changing the medium. The plate is swirled to spread evenly and incubated for 6 hours at 37° C. The medium is changed at the end of the 6 hour transfection, and cells are incubated for another 72 hr.

Regardless of the transfection method used, following the incubation that allows for the synthesis of AAV viral particles, the cells are scraped and both the supernatant and cells are collected. The collected cells are lysed, for example, by four freeze-thaw cycles (alternating between a dry ice-ethanol bath and a 37° C. water bath) and the cell lysates are collected by centrifugation at 10,000×g for 10 min. to remove cell debris. After this centrifugation, the supernatant is ready for viral titration.

AAV Transduction

Transduction by AAV vector particles is measured in standard assays that are well-known in the art. For example, the method described by Russell et al. (1994, Proc. Natl. Acad. Sci. U.S.A. 91: 8915–8919, incorporated herein by reference) works well for monitoring AAV transduction and changes in that process. Briefly, in the standard methods, monolayer cultures of target cells are transduced at a multiplicity of infection of about 0.1 to 10 vector particles per cell (if the vector titer is not known, a range of serial dilutions is used). Cells can be actively proliferating or in stationary phase, depending upon the state desired to be tested for transduction. Following the addition of AAV stock to the target cells, infected cultures are incubated for a period of 2 days to 2 weeks, after which infected cells are detected. Detection is performed in a manner dependent upon the nature of the transgene or marker carried by the AAV vector. For example, transduction of a β-galactosidase marker is detected by applying a chromogenic β-galactosidase substrate (e.g., X-gal), and transduction of a GFP marker is detected by monitoring fluorescence of infected cells. The transduction of other transgenes, for example, therapeutic genes, can be monitored by standard immunohistochemistry staining of infected cells.

The treatment of cells with DNA synthesis inhibitors or topoisomerase inhibitors increases the relative transduction efficiency of AAV (Russell et al., 1995, Proc. Natl. Acad. Sci. U.S.A. 92: 5719–5723). Relative transduction efficiency is an expression of the number of viral transductants per unit volume of AAV particle stock in a culture treated with a DNA synthesis inhibitor, topoisomerase inhibitor and/or an agent that increases the activity of the CMV immediate early promoter, relative to the number of transductants detected when untreated cultures are exposed to the same amount of AAV particle stock. Transduction efficiency is "increased" as used herein when the level of transduction observed in cultures of treated cells is at least 10% greater than the level in untreated cultures. An increase in transduction efficiency in treated cells is preferably at least 20%, 30%, 50%, 75% or more, up to and including 2-fold, 5-fold, 10-fold, 20-fold, 50-fold, 100-fold or more, relative to untreated cells.

While one ultimately wants the most accurate titer possible, the fact that the titer number determined with one assay is different than the titer number obtained for the same viral stock with another assay is not necessarily a problem. It is disclosed herein that the titer determined for a given viral stock increases when target cells are treated with a combination of agents that induce CMV promoter activity and inhibit either DNA synthesis or topoisomerase activity This increase reflects the relative inefficiency of prior art titer methods, in that those methods were not detecting a significant proportion of the infectious particles present. In theory, the titer detected for any viral stock can increase until the titer detected is equal to the actual number of functional viral particles in a sample. A titering assay is preferred that optimizes the detection of functional AAV particles in a sample. The methods and kits of the invention provide equal or superior detection of AAV particles in a sample relative to prior art methods.

DNA Synthesis Inhibition

DNA synthesis inhibitors are demonstrated herein to be useful in improved methods of titering AAV vector particles in a sample. For most purposes, known DNA synthesis inhibitors, such as hydroxyurea, deoxyadenosine, and aphidicolin, among others, can be used in the methods of the invention. The use of known DNA synthesis inhibitors in the methods of the invention requires that one first determine if a given inhibitor functions in the improved titer method. In order to do this, one can perform the titer method as described herein using varying concentrations of the known DNA synthesis inhibitor being tested and a set concentration of AAV virus stock. The assay can be performed on cells treated with an agent that increases the activity of the CMV immediate early promoter, e.g., sodium butyrate. Generally, the concentrations of known DNA synthesis inhibitors used should vary on either side of the concentration known to inhibit DNA synthesis by at least 50%. This titration can be performed in a straightforward manner by varying the concentration of the DNA synthesis inhibitor in an AAV transduction assay using a constant (usually, but not necessarily, known) amount of an AAV reporter vector particle and monitoring the effect of the inhibitor on the level of viral transduction If an increase in the transduction efficiency is detected in the presence, relative to the absence, of the known DNA synthesis inhibitor, that inhibitor is useful according to the methods of the invention.

In the event that one wishes to use an untested or new DNA synthesis inhibitor in a method of the invention, DNA synthesis inhibition is commonly measured by assessing changes in the incorporation of $^3$H-thymidine into DNA by cells cultured in the presence and absence of varying concentrations of the reagent being examined. For example, subconfluent cells of the type to be used for AAV transduction (e.g., HT1080 cells) are either left untreated or exposed to a candidate DNA synthesis inhibitor. Treated and untreated cells are pulse labeled with $^3$H-thymidine and the labeling of the treated versus untreated cells is measured. Methods for measuring $^3$H-thymidine incorporation into DNA are well known in the art and include, for example, autoradiography and scintillation counting of acid precipitated nucleic acid. As used herein, DNA synthesis is "inhibited" if the level in treated cells is at least 10% lower, and preferably 25%, 50%, 75%, or even up to and including 100% (i.e., no DNA synthesis) lower than the level in untreated cells. As used herein, a reagent that inhibits DNA synthesis according to this definition of "inhibited" is a DNA synthesis inhibitor.

An alternative measure of the activity of a given DNA synthesis inhibitor in the methods and kits of the invention is to compare the transduction efficiency in the presence of a DNA synthesis inhibitor being tested with the transduction efficiency in the presence of 40 mM hydroxyurea. A DNA synthesis inhibitor that increases transduction efficiency at least 50% as well as 40 mM hydroxyurea in the titering assay of the invention, but preferably at least as well as or greater than hydroxyurea is a useful DNA synthesis inhibitor according to the invention.

Once one knows whether a candidate DNA synthesis inhibitor is, in fact, an inhibitor as defined above, one can then test the inhibitor for activity in the methods of the invention in the same manner used to test a known DNA synthesis inhibitor.

Topoisomerase Inhibition

Topoisomerases are enzymes that relieve torsional stress on DNA by nicking and religating one or both strands of a supercoiled DNA molecule. DNA topoisomerases whose reactions proceed via a transient single-stranded break and change the linking number in steps of one are classified as type 1, while enzymes whose reactions proceed via double-stranded breaks and changing the linking number in steps of two are classified as type 2. The linking number is a quantitative measure of the number of times one strand crosses the surface of the other strand of a closed circular double-stranded DNA molecule.

Topoisomerase inhibitors can be useful in the titering methods and kits of the invention In order to determine whether a known topoisomerase inhibitor is useful in a titering method or kit of the invention, one can test the inhibitor in much the same manner as described above for testing a DNA synthesis inhibitor. That is, one can perform the AAV titer method as described herein using varying concentrations of the known topoisomerase inhibitor being tested and a set concentration of AAV virus stock. The assay can be performed in cells treated with an agent that increases the activity of the CMV immediate early promoter. Generally; the concentrations of known topoisomerase inhibitors used should vary on either side of the concentration known to inhibit topoisomerase activity by at least 50%. This titration can be performed in a straightforward manner by varying the concentration of the inhibitor in an AAV transduction assay using a constant (usually, but not necessarily, known) amount of an AAV reporter vector particle and monitoring the effect of the inhibitor on the level of viral transduction. If an increase in the transduction efficiency is detected in the presence, relative to the absence, of the known topoisomerase inhibitor, that inhibitor is useful according to the methods of the invention.

Topoisomerase assays suitable for monitoring the activity of type 1 and type 2 topoisomerases are known in the art. For example, the books "*DNA Topoisomerase Protocols Volume I: DNA Topology and Enzymes,* M. Bjornsti and N. Osheroff, Eds., 1999, Humana Press, and *DNA Topoisomerase Protocols, Volume II: Enzymology and Drugs,* N. Osheroff and M. Bjornsti, Eds., 2001, Human Press, both incorporated herein by reference, describe topoisomerase assays. Further, U.S. Pat. No. 6,197,527 (issued Mar. 6, 2001 to Lynch et al.; incorporated herein in its entirety by reference) discloses an assay method based upon the covalent cross linked intermediate that forms between a DNA substrate and a topoisomerase. U.S. Pat. No. 5,656,463 (issued Aug. 12, 1997 to Slesarev, incorporated herein by reference) describes an assay that monitors changes in the migration of a supercoiled plasmid with changes in supercoiling catalyzed by a topoisomerase. Briefly, the Slesarev assay involves the incubation of a 1:1 mixture of positively and negatively supercoiled pBR322 plasmid DNA (0.2 $\mu$g) in assay buffer appropriate for measuring topoisomerase activity (the reference teaches 30 mM Tris, pH 8.0 at 25° C., 1 M potassium glutamate and 5 mM EDTA, but this buffer is optimal for the novel thermophilic topoisomerase disclosed in that patent a more generally applicable assay buffer is 35 mM Tris-HCl (pH 8.0), 72 mM KCl, 5 mM MgCl$_2$, 5 mM DTT, 2 mM spermidine). Reactions are terminated by the addition of SDS, followed by treatment with 400 $\mu$g/ml proteinase K at 37° C. for one hour and heating at 80° C. for two minutes. The products are analyzed on a 1.5% agarose gel in the presence of 1.6 $\mu$g/ml chloroquine at 3 V/cm for 10 hours.

Kits are also available from TopoGEN (Columbus, Ohio) for measurement of topoisomerase activity and for screening agents that inhibit topoisomerase activity. For example, TopoGen's Catalog Nos. 1015-1 and 1000-1 are assay kits for measuring topoisomerase types 1 and 2, respectively. Drug screening kits available from TopoGEN include Catalog Nos. 1018-1 and 1009-1, which permit screening for agents that modify type 1 and type 2 topoisomerase activity, respectively.

Topoisomerase activity is often expressed in terms of the amount required to fully relax a supercoiled standard plasmid in a given amount of time (e.g., the amount necessary to relax supercoiled pBR322 in 30 minutes at 37° C.). Topoisomerase activity is inhibited if its activity is decreased by at least 10% relative to an assay in which no inhibitor is present. A topoisomerase inhibitor useful in the methods and kits of the invention preferably inhibits by 20%, 35%, 50%, 75%, 85%, 90%, 95%, 97%, 99% or even by 100% (no activity) relative to the activity in the absence of the inhibitor.

Once a topoisomerase inhibitor is identified using a topoisomerase assay or assay kit as described herein, that topoisomerase can be tested in an AAV titering assay of the invention exactly as described above for testing a known topoisomerase inhibitor in the assays of the invention. A topoisomerase inhibitor is said to increase AAV transduction efficiency if that efficiency is increased by at least 10% relative to the efficiency observed in the absence of the topoisomerase inhibitor. Transduction efficiency is preferably increased by a topoisomerase inhibitor by at least 25%, 50%, 75% or more, up to and including 2-fold, 5-fold, 10fold, 20-fold, 50-fold, 100-fold or more, relative to the transduction of cells not treated with the inhibitor.

An alternative measure of the activity of a given topoisomerase inhibitor in the methods and kits of the invention is to compare the transduction efficiency in the presence of a topoisomerase inhibitor being tested with the transduction efficiency in the presence of 3 $\mu$M etoposide. A topoisomerase inhibitor that increases transduction efficiency at least 50% as well as 3 μM etoposide in the titering assay of the invention, but preferably at least as well as or greater than 3 μM etoposide is a useful topoisomerase inhibitor according to the invention.

Agents that Increase the Activity of the CMV Promoter

It is demonstrated herein that agents that increase the activity of the CMV promoter are useful in methods and kits for titering AAV particles. Sodium butyrate, for example, induces the CMV promoter and is useful in the disclosed methods and kits. The CMV promoter is induced by a number of agents, such as sodium butyrate, phorbol-12-myristate-13-acetate (PMA), phytohemagglutinin (PHA), forskolin, and dibutyryl cAMP. In order to determine whether a known inducer of the CMV promoter is useful according to the methods and kits of the invention, one can test it by performing an AAV titer assay in cells treated or not treated with that inducer. An increase in transduction efficiency of at least 10% is indicative that the known CMV inducer is useful according to the invention. Preferably the transduction efficiency is increased by at least 20%, 35%, 50%, 75%, 100% or more, including 2-fold, 5-fold, 10-fold, 20-fold, 50-fold, 100-fold or more by a CMV inducer useful according to the invention.

In order to evaluate whether an agent increases the activity of the CMV immediate early promoter, a standard transient transfection promoter assay can be used. For example, a reporter construct in which the CMV major immediate early promoter (−299 to +69, numbered according to the convention of Akrigg et al., 1985, supra) drives the expression of the E. coli lacZ gene or other detectable marker gene can be used. That construct, which should have a eukaryotic polyA addition sequence (e.g., the SV40 polyA addition sequence), is then transiently transfected into cultured cells that are then treated with or without a candidate CMV inducer. An increase of CMV-driven marker activity (e.g., β-galactosidase activity) by at least 10%, preferably 20%, 35%, 50%, 75%, or more, up to and including 2-fold, 5-fold, 10-fold, 20-fold, 50-fold 100-fold or more is indicative that the agent may be useful according to the invention.

Once an agent is found to induce the CMV major immediate early promoter by at least 10 relative to the absence of the agent, that agent should be tested in a range of concentrations in an AAV titer assay as described for agents known to induce the activity of the CMV promoter.

An alternative measure of the activity of an agent that increases the activity of the CMV promoter is to perform an AAV titer assay or a transient transfection assay using various concentrations of the candidate agent in parallel with an assay using 1 mM sodium butyrate. An agent is an agent that increases the activity of the CMV promoter if it produces at least 50% as much detectable marker as the 1 mM sodium butyrate-treated culture. Using this standard of measure, it is preferred that the agent that increases the activity of the CMV promoter induces 75% or more of the level of marker expression induced by 1 mM sodium butyrate, and more preferably 2-fold, 5-fold, 10-fold, 50-fold, 100-fold or more.

It is noted that the CMV promoter contains multiple binding sites for the NF-κB and CREB (cAMP responsive element binding protein) transcription factors. It is contemplated that any agent that increases the binding or activity of either or both of these activities can be useful in an AAV titering method of the invention. For example, TNF-α, proteasome inhibitors, and agents that activate or inhibit kinases or phosphatases in the NF-κB or CREB signal transduction cascades can be useful in an AAV titering method of the invention. One of skill in the art can readily test a given NF-κB or CREB activator for activity in the AAV titering methods of the invention by performing an AAV titer assay in the presence and absence of the agent or by comparing the AAV transduction efficiency in the presence of varying concentrations of the agent with the transduction efficiency in the presence of 1 mM sodium butyrate. An agent that increases the relative transduction efficiency of AAV at least 50% as well as 1 mM sodium butyrate is an agent that increases the activity of the CMV immediate early promoter useful according to the invention.

EXAMPLES

Example 1

Four Plasmid AAV Vector System

The four plasmids were originally from Avigen (Alameda, Calif.). The plasmids were transformed into XL-10 Gold chemical competent cells (Stratagene, Calif.). The transformed cells were plated out on LB/Amp agar plates and incubated overnight at 37° C. A single colony was picked for each plasmid and inoculated in 200 ml of 1×LB/Amp medium. A Maxi-prep was done for each plasmid with Qiagen maxi-filter plasmid purification kit according to manufactorer's protocol. The plasmid DNA pellets were resuspended in T10E1, pH7.5 solution. The authenticity of the purified plasmids was verified by the following methods:

a. Restriction enzyme digestion. One half microgram (0.5 μg) of plasmid DNA was digested with one or two restriction enzyme(s) in a final volume of 10 μl at 37° C. for 2 hours. The digested plasmid samples then were loaded onto 1% TAE agarose gel and the sizes of DNA were visualized under UV light.

b. Sequencing. The plasmid DNAs of p4.1c and pVmLacZ were sequenced by Sequetech (Mountain View, Calif.). The primers p4.1cP1 5'-ATTCTGAGTCCAA GCTAGGC-3' (SEQ ID NO: 1) and p4.1cP2 5'-TAGA AGGACACCTAGTCAGA-3' (SEQ ID NO: 2) were used as sequencing primers for p4.1c. The pVmLacZ sequencing primers were pVmP1 5'-CCTCTGACTTG AGCGTCGAT-3' (SEQ ID NO: 3) and pVmP2 5'-TACTATGGTTGCTTTGACGT-3' (SEQ ID NO: 4).

Verification of the five AAV Vectors by Restriction Endonuclease Digestion

The predicted sizes generated by different restriction enzyme digestions for these four vectors are as follows:

a. p4. 1c; 1.75 kb and 2.73 kb by Not I single digestion; 1.19 kb and 3.3 kb by BamH I and Mlu I double digestions.

b. pVmLacZ: 2.89 kb and 4.38 kb by Not I single digestion; 7.3 kb by ClaI.

c. pHLP19: 0.8 kb and 6.5 kb by BAMH I; 7.3 kb by HindIII.

d. pladeno 5: 2. kb and 9.5 kb by HindIII; 1.71 kb, 1.73 kb (usually appear as one band on the gel because the two bands are too close to be distinguished) and 8.2 kb by EcoR I and Xho I double digestions.

e. pVmhrGFP: 2.44 kb and 2.89 kb by Not I single digestion; 0.75 kb and 4.6 kb by EcoR I and XhoI double digestions.

The observed band sizes of all five AAV vector digests correspond to those predicted.

Sequence verification of p4.1c and pVmLacZ Vectors.

The p4.1c and pVmLacZ vectors were partially sequenced with vector specific primers. The sequences obtained confirmed the authenticity of the vectors.

Construction of pVmhrGFP Vector

The humanized Renilla green fluorescence protein (hrGFP) DNA fragment was excised from plasmid pFB-hrGFP by Xho I and EcoR I and ligated to p4.1c predigested with Xho I and EcoR I enzymes. The p4.1chrGFP and pVmLacZ were digested with Not I, separately, and both the smaller fragments (2.4 kb from p4.1chrGFP and 2.8 kb from pVmLacZ) were gel-purified and religated to form pVmhrGFP.

The sequences of the two identical AAV ITRs, critical to DNA packaging and host chromosomal integration, are GC-rich and repetitive, thus, the sequence integrity of AAV ITRs could only be examined by restriction enzyme digestions (efforts were made to sequence the entire ITRs from both directions with several different primers.) Double digestions with Not I/See 8387 would release both ITRs of 137bp and 145bp along with two large fragments (4384bp and 2605bp) for pVmLacZ and three fragments (1211bp, 1288bp and 2604bp) for pVmhrGFP. The sizes of the two smaller fragments, which are critical in quality control, were ascertained by high percentage agarose or PAGE gel electrophoresis. In addition, any rearrangement, large deletion or even certain mutations of ITRs is detectable by Sma I or Pvu II digestion, which have sites within the ITRs. Digestion by Pvu II would result in 363bp, 429bp, 1303bp, 2557bp and 2619bp fragments for pVmLacZ and 9bp, 139bp, 395bp, 714bp, 1461pb, 2619bp fragments for pVmhrGFP. Digestion of the plasmid by SmaI yielded three fragments of 11bp, 2681bp and 4568bp for pVmLacZ and 11bp, 2625bp and 2681bp for pVmhrGFP.

AAV Viral Vector Production

Cells (293x) were evenly seeded at a density of $3 \times 10^6$ per 10-cm plate containing 10 ml of DMEM, 10%FIBS, 1× glutamine and 1× Penicillin/Streptomycin (C-DMEM), and cultured for 48 hours. On the day of transfection, 1 ml of 0.3M $CaCl_2$ was added to a 15-ml conical tube with 30 μg of plasmids (10 μg each of pHLP19, pladeno 5 and pVmLacZ or pVmhrGFP), mixed gently and the mixture was added drop-wise to another 15-ml tube containing 1 ml of 2×HBS (280 mM NaCl, 50 mM HEPES, 1.5 mm $NaPO_4$, NaOH to pH7.1 exactly), and mixed gently by inversion or gentle vortexing. The suspension was immediately applied drop-wise to the culture plate without changing the medium. The plate was swirled to spread evenly and incubated for 6 hours at 37° C. The medium was changed at the end of the transfection, and cells were incubated for another 72 hr. On the day of virus harvest, the cells were scraped and both the supernatant and cells were collected. The collected cells were lysed by four freeze-thaw cycles (alternating between a dry ice-ethanol bath and a 37° C. water bath) and the cell lysates were collected by centrifugation at 10,000g for 10 min. to remove cell debris. The supernatant is ready for viral titration.

Example 2

AAV Vector Titration i) Titering With Wild-type Adenovirus:

In a 24-well plate, HeLa cells were evenly seeded at a density of $1 \times 10^5$ cells per well in a 0.5 ml volume. A 10-fold series of dilution starting from 5 ul of viral stock per well to 0.00005 ul/well was added to each well of HeLa cells along with wild-type adenovirus-5 (50 virions/cell) and incubated for 20 hours. When the lacZ gene was used a reporter, an in situ beta-galactosidase staining assay was performed using a Stratagene kit (cat#2000384). Briefly, the cells were fixed with 2% formaldehyde and 0.2% glutaraldehyde in PBS for 10 min. at room temperature, washed once with PBS and stained with solution containing 5 mM $K_3Fe(CN)_6$, 5 mM $K_4Fe(CN)_6$, 2 mM $MgCl_2$, and 1 mg/ml x-gal in PBS overnight at 37° C. The blue cells were counted at appropriate dilution.

ii) Titering Without Adenovirus:

HT1080 cells were evenly seeded in a 12-well plate at a density of $1.5 \times 10^5$ cells/well in 1 ml of C-DMEM 1 day prior to assay (care was taken to avoid a condensed center). On the day of the assays, 0.2 ml of C-DMEM with 240 mM of hydroxyurea (HU) and 6 mM of sodium butyrate (NaB) was added to each well without changing the medium bringing the final connectrations to 40 mM HU and mM NaB. (Hu stock: 1M in PBS, sterile by filtration; NaB stock: 0.5 M in PBS, sterile by filtration). The medium was mixed well and the plate was incubated at 37° C. for 5–6 hours. The cells were washed once with prewarmed L-DMEM (DMEM with 2% FBS and 1×glu) before adding 0.5 ml of viral media into each well, staring from 10 μl of crude viral stock in 1 ml L-DMEM to 0.01 μl in 1 ml. Each sample had triplicates. The cells were incubated at 37° C. for 1–2 hours, swirling 2–3 times. Another 0.5 ml of prewarmed H-DMEM (DMEM with 18% FBS and 1× glu) was added to each well and the cells were incubated for 2 days (40–48 hours). When lacZ was used as a reporter, an in situ beta-galactosidase staining assay was performed using a Stratagene kit (cat#2000384) to visualize infected cells. When the hrGFP gene was used as a reporter, FACS analysis was performed. (Cytometry Research, LLC, San Diego, Calif.). The number of cells expressing the detectable marker is directly proportional to the number of viral particles per ml present in the AAV stock being titered.

AAV Titering Results

The AAV-LacZ and AAV-GFP vector stocks were prepared as described above and the titers of the viral stocks were determined by either co-infecting HeLa cells with wild-type Adenovirus-5 or infecting HT1080 cells treated with a DNA synthesis inhibitor (Hu) and an agent that increases CMV immediate—early promoter activity (NaB; see Table 2). HeLa cells and Ad-5 infection were used for titering, the titer was of $1.7 \times 10^8$ infectious virus (i.v.)/ml as calculated from 0.5 ml vector stock per well. The titer, calculated based on 0.05 μl vector stock per well, was higher, at $4.3 \times 10^8$ i.v./ml, but, was still within the same $10^8$ log scale. Preliminary data using quantitative-polymerase chain reaction (Q-PCR) indicated that the absolute vector titer was at more than $10^{10}$ viral genomes/ml. That is, there were more than $10^{10}$ vector particles per ml by Q-PCR There is no assumption, however, that all particles are infectious. All titer data obtained above were from experiments done on a 10-cm plate, that contained a total of 30 μg of DNA (all three vectors). The total volume of crude extract was 10 ml per 10-cm plate. These data were in agreement with the titers predicted by Avigen.

TABLE 2

AAV Viral Titers

| Exp.# | Reporter | Titer Method | Stock Dil. (ml) | Apparent Titer (VP/ML) |
|---|---|---|---|---|
| 1 | B-galactosidase | Ad infection | $5 \times 10^{-4}$ | $1.7 \times 10^8$ |
|   | "                |              | $5 \times 10^{-5}$ | $4.3 \times 10^8$ |
| 2 | "                | Na But. + HU | $5 \times 10^{-4}$ | $2.8 \times 10^8$ |
|   | "                | No Treatment | $5 \times 10^{-4}$ | $2.1 \times 10^7$ |
| 3 | HrGFP            | "            | $5 \times 10^{-3}$ | $0.9 \times 10^7$ |
|   | "                | "            | $5 \times 10^{-3}$ | $1.0 \times 10^7$ |
|   | "                | Na But. + HU | $5 \times 10^{-4}$ | $4.6 \times 10^7$ |
|   | "                | "            | $5 \times 10^{-4}$ | $5.5 \times 10^7$ |

Experiment 1: In a 24-well plate, $1 \times 10^5$ HeLa cells were evenly seeded in each well in a 0.5 ml volume. The next day, a 10-fold serial dilution was made, starting from 5 µl of viral stock (out of 10 ml) per well to a final of 0.00005µl/well with wild-type adenovirus 5 (50 virions/cell).

Experiment 2: One day before titering, HT1080 cells were evenly seeded in a 12-well plate at $1 \times 10^5$ cells/well in 1 ml of C-DMEM. On the day of titering, as chemical treatment, 0.2 ml of C-DMEM with 240 mM of hydroxyurea (Hu) and 3 mM of sodium bytyrate (NaB) were added into each well without changing the medium. The medium was mixed well and the plate was incubated at 37° C. for 5–6 hours. Both control and treated cells were washed once with prewarmed L-DMEM (DMEM with 2% FBS and 1× glu) before adding 0.5 ml of viral media into each well, starting from 10 µl of crude viral stock in 1 ml L-DMEM to 0.01 µl in 1 ml. The cells were incubated at 37° C. for 1–2 hours, swirling 2–3 times. Another 0.5 ml of prewarmed H-DMEM (DMEM with 18% FBS and 1× glu) was added to each well and the cells were incubated for 2 days (40–48 hours). For both experiments, in situ beta-galactosidase staining assay was performed 20 hours after infection and the blue cells were counted in the wells of either 0.5ul or 0.05 ul/well. Several areas in each well were counted in order to obtain an average number of calculation using the formula of Viral titer= (average# of blue cells)×(whole well area factor)×(dilution factor). For experiments involving the hrGFP reporter, titers were determined by flow cytometry and calculated using the formula (% fluorescent cells in gated population)×(total number of cells infected)'(dilution).

Traditionally, methods to titer AAV infections viral particles involve wild-type adenovirus co-infection. A diluted vital stock is added to Ad-infected cells and the titer is determined one or two days later by various methods depending upon which reporter gene is used. The LacZ gene is the most popular reporter, alkaline phosphatase and GFP are also commonly used as reporters. The requirement for wild-type Ad co-infection is a drawback of the traditional titering method. Without Ad co-infection, however, the titering process could take more than a week to potentially a month to obtain optimal marker protein expression at a measurable level with certain cell types. In addition, the titer number obtained from methods without Ad co-infection is usually lower than that from the one with Ad co-infection, so it was clear that an improved helper-free titering method is necessary.

A titering protocol is developed herein which not only has a lower toxicity to the cells used but also gives higher transduction efficiency. It was discovered that HT1080 cells, treated with 40 mM hydroxyurea and 1 mM sodium bytyrate, were more permissive to the AAV transduction. The same viral stock used in HeLa cells with Ad-5 coinfection was titered again with this new Ad-free method and the titer was at $2.8 \times 10^8$ i.v./ml, while the untreated Ad-free control was more than ten fold less at only $0.21 \times 10^8$ i.v./ml (Table 2). This new method gave results comparable to that generated by the commonly used Ad-co-infection method (See Table 2 for comparison).

This titering method has also been performed in HeLa and HT1080 cells using an hrGFP reporter (data not shown). This method has also been used successfully on 293X cells, and RBL cells with either hrGFP or LacZ reporters (data not shown). The mechanism behind altered transduction efficiency of AAV by chemical treatments is currently unclear. One study with gamma radiation showed that neither increased gene expression nor episomal vector DNA amplification accounted for increased transduction efficiency (Alexander et al., 1994, J. Viral, 68: 8282–8287). Another study observed that chemicals that affected DNA metabolism, but not transcription, protein translation or mitotic spindle formation, could enhance transduction by AAV vectors (Russell et al., 1995, Proc. Natl. Acad. Sci. U.S.A. 92: 5719–5723). It was hypothesized that damaged DNA might provide sites for vector DNA integration or would lead to induction of repair enzymes, such as DNA polymerases, and induction of factors modulating cell cycle progression that increase AAV vector transduction. Knowledge of the mechanism of DNA synthesis inhibitors, topoisomerase inhibitors and CMV promoter inducing agents in increased viral transduction efficiency is not, however, critical to the claimed invention. What is critical is that a DNA synthesis inhibitor and an agent that increases CMV promoter activity are advantageous in a method of obtaining an AAV titer more accurately and more rapidly than is possible without those agents.

Example 3

AAV Titering in the Cells Treated with Topoisomerase Inhibitor And CMV Promoter Inducing Agent DNA synthesis inhibitors are not the only agents capable of increasing the transduction efficiency or the titering efficiency of AAV particles. Topoisomerase inhibitors, such as etoposide and camptothecin can be used in conjunction with an agent that induces the CMV promoter to provide an improved AAV titer method.

To titer AAV in cells treated with a topoisomerase inhibitor and an agent that induces the CW immediate early promoter, HT1080 cells (or other target cells) are evenly seeded in a 12-well plate at $1.5 \times 10^5$ cells/well in 1 ml of C-DMEM. The next day, the cells are treated with the topoisomerase inhibitor and an agent that increases the activity of the CMV promoter. For example, 0.2 ml of C-DMEM with 18 µM etoposide and 6 mM of sodium butyrate (NaB) is added to each well without changing the medium, for a final concentration of 3 µM etoposide and 1 mM sodium butyrate. The medium is mixed well and the plate is incubated at 37° C. for 5–6 hours. The cells are washed once with prewarmed L-DMEM (DMEM with 2% FBS and 1×glu) before adding 0.5 ml of viral media into each well, starting from 10 µl of crude viral stock in 1 ml L-DMEM to 0.01 in 1 ml. Titration is performed using triplicate dilution samples. The cells are incubated at 37° C. for 1–2 hours, swirling 2–3 times. Another 0.5 ml of prewarmed H-DMEM (DMEM with 18% FBS and 1×glu) is added to each well and the cells are incubated for 2 days (40–48 hours). When lacZ is used as a reporter, an in situ beta-galactosidase staining assay is performed using, for example, a Stratagene kit (cat#2000384) for titration. When, alternatively, the hrGFP gene is used as a reporter, FACS analysis is performed (Cytometry Research, LLC, San Diego, Calif.).

If desired, the topoisomerase-inhibitor plus CMV promoter-inducing agent titer assay can be performed in parallel with a titer assay using Adenovirus in order to compare the resulting titers. It is anticipated that the titer from the topoisomerase inhibitor plus CMV inducer assay will be at least as high as that using Adenovirus co-infection. Alternatively, the topoisomerase inhibitor plus CMV inducer titer assay can be compared with a DNA synthesis inhibitor plus CMV promoter inducing agent titer assay (e.g., an assay using hydroxyurea and sodium butyrate treatment of the cells). It is anticipated that the titer determined with the assay using the topoisomerase inhibitor (plus CMV inducer) will be at least 50% as high as the titer determined using the DNA synthesis inhibitor (plus CMV inducer). It is preferred that the titer is the same as that obtained with the DNA synthesis inhibitor, or more preferably, that the titer obtained using the topoisomerase-treated cells is even higher than that obtained with the DNA synthesis inhibitor-treated cells. One skilled in the art can use the present disclosure and skill in the art to optimize the concentration and times of exposure to the topoisomerase and CMV promoter inducer.

What is claimed is:

1. A method of titering adeno-associated virus particles in a sample, said method comprising the steps of:
   a) contacting target cells with a DNA synthesis inhibitor and an agent that increases the activity of the CMV immediate early promoter;
   b) contacting target cells treated as in step (a) with a sample containing adeno-associated virus particles; and
   c) determining the number of target cells infected by said adeno-associated virus particles in said sample, wherein said number of target cells infected is directly proportional to the titer of said particles in said sample, thereby determining the titer of said adeno-associated virus particles.

2. The method of claim 1 wherein said target cells are not infected with adenovirus.

3. The method of claim 1 wherein said DNA synthesis inhibitor is selected from the group consisting of: hydroxyurea and aphidicolin.

4. The method of claim 3 wherein said DNA synthesis inhibitor is hydroxyurea.

5. The method of claim 4 wherein said hydroxyurea is present in step (b) at a concentration in the range of 20 mM to 80 mM, inclusive.

6. The method of claim 4 wherein said hydroxyurea is present in step (b) at a concentration of 40 mM.

7. The method of claim 1 wherein said agent that increases the activity of the CMV immediate early promoter is selected from the group consisting of: sodium butyrate, dibutyryl cAMP, phorbol-12-myristate-13 acetate (PMA), phytohemagglutinin (PHA) and forskolin.

8. The method of claim 7 wherein said agent that increases the activity of the CMV immediate early promoter is sodium butyrate.

9. The method of claim 8 wherein said sodium butyrate is present in step (b) at a concentration in the range of 0.2 mM to 2.0 mM, inclusive.

10. The method of claim 8 wherein said sodium butyrate is present in step (b) at a concentration of 1 mM.

11. The method of claim 1 wherein said DNA synthesis inhibitor is hydroxyurea and said agent that increases the activity of the CMV immediate early promoter is sodium butyrate.

12. The method of claim 11 wherein said hydroxyurea is present in step (b) at a concentration in the range of 20 mM to 80 mM, inclusive, and said sodium butyrate is present in step (b) at a concentration in the range of 0.2 mM to 2.0 mM, inclusive.

13. The method of claim 11 wherein said hydroxyurea is present in step (b) at a concentration of 40 mM and said sodium butyrate is present in step (b) at a concentration of 1 mM.

14. The method of claim 1 wherein after step (a) and before step (b), said DNA synthesis inhibitor and said agent that increases the activity of the CMV immediate early promoter are substantially removed.

15. A method of titering adeno-associated virus particles in a sample, said method comprising the steps of:
   a) contacting target cells with a topoisomerase inhibitor and an agent that increases the activity of the CMV promoter;
   b) contacting target cells treated as in step (a) with a sample containing adeno-associated virus particles; and
   c) determining the number of target cells infected by said adeno-associated virus particles in said sample; wherein said number of target cells infected is directly proportional to the titer of said particles in said sample, thereby determining the titer of said adeno-associated virus particles.

16. The method of claim 15 wherein said target cells are not infected with adenovirus.

17. The method of claim 15 wherein said topoisomerase inhibitor is selected from the group consisting of: etoposide and camptothecin.

18. The method of claim 17 wherein said topoisomerase inhibitor is etoposide.

19. The method of claim 18 wherein said etoposide is present in step (b) at a concentration in the range of 0.5 uM to 5.0 uM, inclusive.

20. The method of claim 18 wherein said etoposide is present in step (b) at a concentration of 3 $\mu$M.

21. The method of claim 15 wherein said agent that increases the activity of the CMV immediate early promoter is selected from the group consisting of: sodium butyrate, dibutyryl cAMP, forskolin, phytohemagglutinin (PHA) and pharbol-12-myristate-13-acetate (PMA).

22. The method of claim 21 wherein said agent that increases the activity of the CMV immediate early promoter is sodium butyrate.

23. The method of claim 22 wherein said sodium butyrate is present in step (b) at a concentration in the range of 0.2 mM to 2.0 mM, inclusive.

24. The method of claim 23 wherein said sodium butyrate is present in step (b) at a concentration of 1 mM.

25. The method of claim 15 wherein said topoisomerase inhibitor is etoposide and said agent that increases the activity of the CMV immediate early promoter is sodium butyrate.

26. The method of claim 25 wherein said hydroxyurea is present in step (b) at a concentration in the range of 2.0 mM to 80 mM, inclusive, and said sodium butyrate is present in step (b) at a concentration in the range of 0.2 mM to 2.0 mM, inclusive.

27. The method of claim 25 wherein said hydroxyurea is present in step (b) at a concentration of 40 mM and said sodium butyrate is present in step (b) at a concentration of 1 mM.

28. The method of claim 15 wherein after step (a) and before step (b), said DNA synthesis inhibitor and said agent that increases the activity of the CMV immediate early promoter are substantially removed.

29. A kit for determining the titer of AAV vector particles in a sample, the kit comprising a DNA synthesis inhibitor and an agent that increases the activity of the CMV immediate early promoter, and packaging materials therefor.

30. The kit of claim 29 wherein said DNA synthesis inhibitor is selected from the group consisting of: hydroxyurea and aphidicolin.

31. The kit of claim 29 wherein said DNA synthesis inhibitor is hydroxyurea.

32. The kit of claim 29 wherein said agent that increases the activity of the CMV immediate early promoter is selected from the group consisting of: sodium butyrate, dibutyryl cAMP, forskolin phytohemagglutinin (PHA) and pharbol-12-myristate-13-acetate (PMA).

33. The kit of claim 29 wherein said agent that increases the activity of the CMV immediate early promoter is sodium butyrate.

34. A kit for determining the titer of AAV vector particles in a sample, the kit comprising an AAV vector system, a DNA synthesis inhibitor and an agent that increases the activity of the CMV immediate early promoter, and packaging materials therefor.

35. The kit of claim 34 wherein said DNA synthesis inhibitor is selected from the group consisting of: hydroxyurea and aphidicolin.

36. The kit of claim 34 wherein said DNA synthesis inhibitor is hydroxyurea.

37. The kit of claim 34 wherein said agent that increases the activity of the CMV immediate early promoter is selected from the group consisting of: sodium butyrate, dibutyryl cAMP, forskolin phytohemagglutinin (PHA) and pharbol-12-myristate-13-acetate (PMA).

38. The kit of claim 34 wherein said agent that increases the activity of the CMV immediate early promoter is sodium butyrate.

39. A kit for determining the titer of an AAV vector particle in a sample, the kit comprising a topoisomerase inhibitor, an agent that increases the activity of the CMV immediate early promoter and packaging materials therefor.

40. The kit of claim 39 wherein said topoisomerase inhibitor is selected from the group consisting of: camptothecin and etoposide.

41. The kit of claim 39 wherein said topoisomerase inhibitor is etoposide.

42. The kit of claim 39 wherein said agent that increases the activity of the CMV immediate early promoter is selected from the group consisting of: sodium butyrate, dibutyryl cAMP, forskolin phytohemagglutinin (PHA) and pharbol-12-myristate-13-acetate (PMA).

43. The kit of claim 39 wherein said agent that increases the activity of the CMV immediate early promoter is sodium butyrate.

44. A kit for determining the titer of an AAV vector particle in a sample, the kit comprising an AAV vector system, a topoisomerase inhibitor, an agent that increases the activity of the CMV immediate early promoter and packaging materials therefor.

45. The kit of claim 44 wherein said topoisomerase inhibitor is selected from the group consisting of: camptothecin and etoposide.

46. The kit of claim 44 wherein said topoisomerase inhibitor is etoposide.

47. The kit of claim 44 wherein said agent that increases the activity of the CMV immediate early promoter is selected from the group consisting of: sodium butyrate, dibutyryl cAMP, forskolin phytohemagglutinin (PHA) and pharbol-12-myristate-13-acetate (PMA).

48. The kit of claim 44 wherein said agent that increases the activity of the CMV immediate early promoter is sodium butyrate.

\* \* \* \* \*